(12) United States Patent
Cone et al.

(10) Patent No.: US 6,355,235 B1
(45) Date of Patent: Mar. 12, 2002

(54) TOPICAL APPLICATION OF ANTIBODIES FOR CONTRACEPTION AND FOR PROPHYLAXIS AGAINST SEXUALLY TRANSMITTED DISEASES

(75) Inventors: Richard A. Cone; Kevin J. Whaley, both of Baltimore, MD (US)

(73) Assignee: Johns Hopkins University, Baltimore, MD (US)

(*) Notice: Subject to any disclaimer, the term of this patent is extended or adjusted under 35 U.S.C. 154(b) by 0 days.

(21) Appl. No.: 09/447,411

(22) Filed: Nov. 23, 1999

Related U.S. Application Data

(62) Division of application No. 08/011,837, filed on Feb. 1, 1993, now Pat. No. 6,045,786, which is a continuation of application No. 07/305,048, filed on Feb. 1, 1989, now abandoned.

(51) Int. Cl.[7] .................. A61K 31/74; A61K 39/395; A61K 39/00; A61K 39/40
(52) U.S. Cl. ................. 424/78.02; 424/811; 424/78.07; 424/134.1; 424/150.1; 424/158.1; 514/841; 514/843
(58) Field of Search ................ 424/87, 78.02, 424/134.1, 150.1, 158.1, 28.07, 811; 514/841, 843

(56) References Cited

U.S. PATENT DOCUMENTS 4,652,448 A * 3/1987 Sadowski .................... 424/87

OTHER PUBLICATIONS

Touchette, N. (1991) AIDS research and mucosal immune studies begin to gel. J. NIH Rep. 3:65–70.
Forrest, B.D. (1991) Women, HIV and mucosal immunity. Lancet 337:835–836.
Nowak, R. (1991) AIDS vaccines: key questions still unanswered. J. NIH Res. 3:37–39.
Sabin, A. (1991) Effectiveness of AIDS Vaccines. Science 251:1161.
Isojima, S. et al. (1987) Establishment and characterization of a human hybridoma secreting monoclonal antibody with high titers of sperm immobilizing and agglutinating activities against human seminal plasma. J. Reprod. Immun. 10:65–78.
Isojima, S. (1989) Human sperm antigens corresponding to sperm–immobilizing antibodies in the sera of women with infertility of unknown cause: personal review of our recent studies, Human Reprod. 4:605–612.
Iosjima, S. (1990) Sperm and seminal plasm antigens relevant to contraceptive vaccine development, Curr. Opin. Immun. 2:752–756.
Herr, J.C. et al. (1986) Characterization of a monoclonal antibody to a conserved epitope on human seminal vesicle–specific peptides: a novel probe/marker system for semen identification, Biol. Reprod. 35:773–784.

Menge, A.C. et al. (1987) Characterization of monoclonal antibodies against human sperm antigens by immunoassays including sperm function assays and epitope evaluation, Am. J. Reprod. Immun. Microbio. 13:108–114.
Bandivdekar, A.H. et al. (1987) Antibodies to human seminal plasma inhibin cause sperm agglutination and impairment of cervical mucus penetration and sperm–egg attachment, Adv. Contracept. 3:1–12.
Hekman. A., Rumke P. (1969) the antigens of human seminal plasma (with special reference to lactoferrin as a spermatozoa–coating antigen), In: Proteins or Biological Fluids 16:549–552.
Vuento, M. et al. (1984) Characterization of fibronectin on human spermatozoa, Hoppe–Seyler's Z Physiol. Chem. 365:757–762.
Glander, H.J. et al. (1987) The equatorial fibronectin band (EFB) on human spermatozoa—a diagnostic help for male fertility? Andrologia 19:456–459.
Goodman, S.A., Young L.G. (1981) Immunological identification of lactoferrin as a shared antigen on radioiodinated human sperm surface and in radioiodinated human seminal plasma. J. Reprod. Immuno. 3:99–108.
Kamada, M. et al. (1991) Identification of IgG and Fc–binding proteins in human seminal plasma and sperm. Arch. Andro. 27:1–7.
Abrescia, P. et al. (1985) Identification and preliminary characterization of a sperm–binding protein in normal human semen. J. Reprod. Fert. 73:71–77.
Saji, F. et al. (1986) Further characterization of a human sperm coating antigen (gp12), Am. J. Reprod. Immun. Microbiol. 12:13–16.
Fellous, M. et al. (1976) The expression of human beta2–microglobulin on human spermatozoa, Eur. J. Immunol. 6:21–24.
Voglmayr, J.K. et al. (1986) Surface transformation of ram spermatozoa in uterine, oviduct and cauda epididymal fluids in vitro, J. Reprod. Fert. 78:315–325.

(List continued on next page.)

Primary Examiner—Theodore J. Criares
(74) Attorney, Agent, or Firm—Venable; Ann S. Hobbs

(57) ABSTRACT

Certain antibody molecules are so stable and so potent at immobilizing sperm as well as the pathogens for sexually transmitted diseases (STDs) that they make possible new prophylactic contraceptive methods: (a) for men, a skin lotion containing antibodies against sperm and against STD pathogens to be applied to the penis and external genitals during sexual activity, thereby delivering prophylactically effective doses of antibodies to virtually all areas of skin and epithelia across which most STDs, including AIDS, are usually transmitted, and, during vaginal intercourse, the penis will deliver a contraceptively reliable dose of the antibodies to the cervical region of the vagina; and (b) for women, intrauterine devices (IUDs) and intravaginal devices (IVDS) that release antibodies into the uterus or into the vagina to provide continuous protection against pregnancy and STDs for periods of months to years.

12 Claims, 3 Drawing Sheets

OTHER PUBLICATIONS

Ceri. H., et al. (1988) Host binding proteins and bacterial adhesion: ecology and binding model, Biochem. Cell. Biol. 66:541–548.

Ouaissi, M.A. (1988) Role of the RGD sequence in parasite adhesion to host cells, Parasit, Today 4:169–173.

Baughn R.E. (1987) Role of fibronectin in th epathogenesis of syphilis, Rev. Infect. Dis. 9:S372–S385.

Peterson, K.M. et al. (1983) Treponema pallidum receptor binding proteins interact with fibronectin, J. Exp. Med. 157:1958–1970.

Alderette, J.F. et al. (1979) Surface–associated host proteins on virulent Treponema pallidum, Inf. Immun. 26:1048–1056.

Baughn, R.E. (1990) Demonstration and immunochemical chracterization of natural, autologous anti–idiotypic antibodies throughout the course of experimental syphilis, Inf. Immun. 58:766–773.

Peterson, K.M. et al. (1984) Iron uptake and increased intracellular enzyme activity follow host lactoferrin binding by Trichomonias vaginalis receptors, J. Exp. Med. 160:398–410.

Peterson, K.M. et al. (1984) Selective acquisition of plasma proteins by Trichomonas vaginalis and human lipoproteins as a growth requirement for this species, Mol. Biochem. Parasit. 12:37–48.

Peterson, K.M. et al. (1982) Host plasma proteins on the surface of pathogenic Trichomonas vaginalis, Inf. Immuno. 37:755–762.

Levy, J.A. (1988) The transmission of AIDS: the case of the infected cell, JAMA 259:3037–3038.

Meltzer, M.A. et al. (1990) Role of mononuclear phagocytes in the pathogenesis of human immunodeficiency virus infection, Annu. Rev. Immunol. 8:169–194.

Gartner, S. et al. (1986) The role of mononuclear phagocytes in HTLV–III/LAV infection, Science 222:215–219.

Wells, C.L. et al. (1988) Proposed mechanisms for the translocation of intestinal bacteria, Rev. Inf. Dis. 10:958:979.

Frank, U. et al. (1978) Multiplication of herpes simplex virus types 1 and 2 in macrophages of NMRI and C57/BL mice, Acta Virol. 22:193–202.

Lopez, C. et al. (1979) Replication of herpes simplex virus type 1 in macrophages from resistant and susceptible mice, Inf. Immun. 23:432–437.

Kuo, C–C. (1978) Cultures of Chlamydia trachomatis in mouse peritoneal macrophages: factors affecting organism growth, Inf. Immun. 20:439–445.

Shafer, W.M. et al. (1989) Interactions of gonococci with phagocytic cells, Annul. Rev. Microgiol. 43:121–145.

Toth, A. (1987) The role of spermatozoa in the development of pelvic inflammatory disease in the woman, Adv. Contracept. 3:97–102.

Baccetti, B. et al. (1991) HIV particles detected in spermatozoa of patients with AIDS, J. Submicrosc. Cytol. Pathol. 23:339–345.

Hill, A.C. (1991) Mycoplasma spermatophilum, a new species isolated from human spermatozoa and cervis, Int. J. System. Bact. 41:229–233.

Howard, T.L. (1971) Bacterial hitch–hikers, J. Urol. 106:94.

Huang, E–S., et al. (1986) Molecular epidemiology and oncogenicity of human cytomegalovirus, Biochem. Mol. Epi. Cancer 323–344.

Atkinson, P.W. et al. (1991) Association of exogenous DNA with cattle and insect spermatozoa in vitro, Mol. Reprod. Devel. 29:1–5.

Brackett, B.G., et al. (1971) Uptake of heterologous genome by mammalian spermatozoa and its transfer of ova through fertilization, Proc. Nat. Acad. Sci. 68:353–357.

Smiley, L., et al. (1990) Cytomegalovirus as a sexually transmitted infection, In Holmes K.K., Mardh, P–A, Sparling, P.F., Wiesner, P.J. (eds.) Sexually Transmitted Diseases, McGraw–Hill, New York, pp. 415–423.

Miller, V.E. et al. (1990) Transfer of HIV by semen: role of sperm In: Alexander, N.J., Gabelmick, H.L.I. Spieler, J.M. (eds.) Heterosexual Transmission of AIDS, Wiley–Liss, New York, pp. 147–154.

Wolner, Hanssen P., et la. (1984) In vitro test of the adherence of chlamydia trachomatis to human spermatozoa, Fert. Steril. 42:102–107.

Benosit, C. et la. (1989) Sperm cells as vectors for transferring DNA into mouse eggs: a breakthrough for immunologists. Immun. Today 10:369.

Taylor–Robinson et al. (1967) Spermadsorption and spermagglutination by mycoplasmas, Nature 215:484–487.

Toth, A. et al. (1982) Evidence for microgial transfer by spermatozoa, Obstet. Gyn. 59:556–559.

Kiessling, A.A. et la. (1987) Sperm–associated retroviruses in th emouse epididymis, Proc. Natl. Acad. Sci. USA 84:8667–8671.

Gobert, B. et al. CD4–like molecules in human sperm, FEBS 261:339–342.

Lingwood, C.A. et al. (1990) Common sulfogylcolipid receptor for mycoplasmas involved in animal and human infertility, Biol. Reprod. 43:694–697.

Pearce, W.A. et al. (1978) Attachment role of gonococcal pili. Optimum conditions and quantitation of adherence of isolated pili to human cells in vitro, J. Clin. Invest. 61:931–943.

Gnarpe, H. et al. (1973) T Mycoplasmas on spermatozoa and infertility, Nature 245:97–98.

Dimmock. N.J. (1987) Multiple mechanisms of neutralization of animal viruses, TIBS 12:70–75 (see especially the summary of possible mechanisms in Table I, p. 73).

Armstrong, S.J. et al. (1990) Morphological studies of the neutralization of influenza virus by IgM. J. gen. Virol. 71:2313–2319.

Outlaw, M.C. et al. (1990) Mechanisms of neutralization of influenza virus on mouse tracheal epithelial cells by mouse monoclonal polymeric IgA and pyllyclonal IgM directed against the viral haemagglutinin, J. gen. Virol. 71:69–76.

Biesbrock, A.R. et al. (1991) Interaction of a salivary mucin–secretory immunoglobulin A. complex with mucosal pathogens, Inf. Immun. 59:3492–3497.

Clamp, J.R. (1977) The relationship between secretory immunoglobulin A and mucus, Biochem. Soc. Trans. 5:1579–1581.

Magnusson, K.E. et al. (1982) Mucosal barrier mechanisms, Interplay between secretory IgA (SIgA), IgG and mucins on the surface properties and association of salmonellae with intestine and granulocytes, Immunology 45:239–248.

Williams, R.c. et al. (1972) Inhibition of bacterial adherence by secretory immunoglobulin A: A mechanism of antigen disposal, Science 177:697–699.

Stokes, C.R. et al. (1975) Immune exclusion is a function of IgA, Nature 255:745–746.

Carlisle, M.S. et al. (1990) The role of mucus in antibody-mediated rapid expulsion of Trichinella spiralis in suckling rats, Immunology 70:126–132.

Samra, H.K. et al. (1991) Human milk containing specific secretory IgA inhibits binding of giardia lamblia to nylon and glass surfaces, J. Diarrhoeal Dis. Res. 9:100–103.

Kremer, J. et al. (1983) The inhibition of sperm penetration in cervical mucus of women with antispermatozoa antibodies, In: Immunological Factors in Human Contraception. Ed. By S. Shulman and F. Dondero, Acta Medica, pp. 147–160.

Raff, H.V. et al. (1991) Comparison of functional activities between IgGI and IgM class–switched human monoclonal antibodies reactive with group B streptococci or *Eschericia coli* K1, J. Infect. Dis. 163:346–354.

Tacket, C.O. et al. (1988) Protection by milk immunoglobulin concentrate against oral challenge with enterotoxigenic *Escherichia coli*. N. Engl. J. Med. 318:1240–1243.

Brambell, F.W.R. (1970) The Transmission of Passive Immunity from Mother to Young, North–Holland Publishing Co., Amsterdam.

Eibl., M.M. et al. (1990) Prophylaxis of necrotizing enterocolitis by oral IgA–IgG: Review of a clinical study in low birth weight infants and discussion of the pathogenic role of infection, J. Clin. Immun. 10:72A–79S.

Glass, R.I. et al. (1983) Protection against cholera in breast–fed children by antibodies in breast milk, N. Engl. J. Med. 308:1389–1392.

Tamura, S. et al. (1991) Cross–protection against influenza A virus infection by passively transferred respiratory tract IgA antibodies to different hemagglutinin molecules, Eur. J. Immunol. 21:1337–1344.

Renegar, K.B. et al. (1991) Passive transfer of local immunity to influenza virus infection by IgA antibody, J. Immun. 146:1972–1978.

Raff, H.V. et al. (1988) Human monoclonal antibody with protective activity for *Eschericia coli* K1 and Neisseria meningitidis Group B infections, J. Infect. Dis. 157:118–126.

Tamura, S. et al. (1990) Functional role of respiratory tract haemagglutinin–specific IgA antibodies in protection against influenza, Vaccine 8:479–485.

Pincus, S.H. et al. (1988) Protective efficacy of IgM monoclonal antibodies in experimental group B streptococcal infection is a function of antibody avidity, J. Immun. 140:2779–2785.

Bessen, D. et al. (1988) Passive acquired mucosal immunity of group A streptococci by secretory immunoglobulin A.J. exp. Med. 167:1945–1950.

Mazanec, M.B. et al. (1987) Immunoglobulin A. monoclonal antibodies protect against Sendai Virus, J. Virol. 61:2624–2626.

Hafez, E.S.E. (1976) human semen and fertility regulation in men. The C.V. Mosby Company, Saint Louis. Appendices 598–599.

Huang, E–S. (1984) The Role of Cytomegalovirus Infection in Kaposi's Sarcoma, In: Friedman–Kien, A.E. (eds.) AIDS: The Epidemic of Kaposi's Sarcoma, New York.

Kurono, Y. et al. (1991) Inhibition of Bacterial Adherence by Nasopharyngeal Secretions, Ann. Otol. Rhinol. Laryngol. 100:455–458.

James–Holmquest, A.N. (1974) Differential attachment by piliated and nonpiliated Neisseria gonorrhoeae to human sperm. Infect. Immun. 9:897–902.

Levy, J.A. (1980) Mouse sperm can horizontally transmit type C viruses, J. Gen. Virol. 51:439–443.

Isojima et al. J. Reprod. Imm. 10 (1987) pp. 67–78.

Herr et al. Biol. Of Reprod. 32 (1985) pp. 695–711.

Mettler et al. American J. of Reprod. Imm. 5 (1984) pp. 125–128.

* cited by examiner

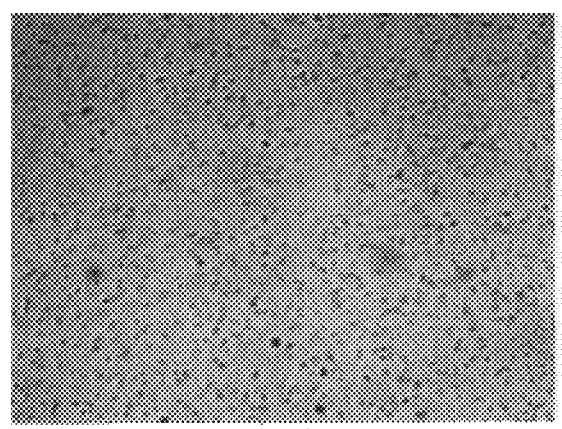
Control
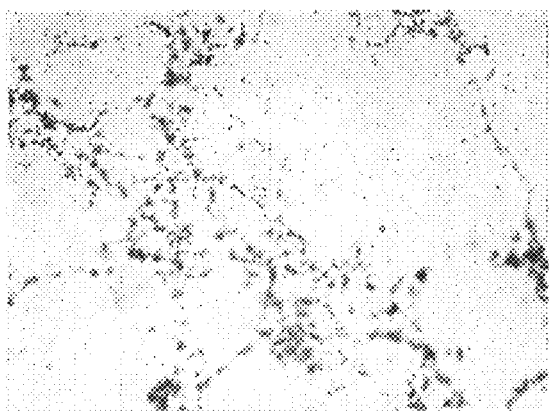
IgG MHS-8 at 100 ug/ml
IgM H6-3C4 at 0.1 ug/ml

TOPICAL APPLICATION OF ANTIBODIES FOR CONTRACEPTION AND FOR PROPHYLAXIS AGAINST SEXUALLY TRANSMITTED DISEASES

This is a continuation of application Ser. No. 08/011,837, filed Feb. 1, 1993 now U.S. Pat. No. 6,045,786 which is a continuation of application Ser. No. 07/305,048 filed Feb. 1, 1989, abandoned.

BACKGROUND OF THE INVENTION

1. Technical Field

This invention describes methods of contraception and prophylaxis against sexually transmitted diseases (STDs), including acquired immunodeficiency syndrome (AIDS), and compositions and devices for use in such methods.

2. Background Information

There is an urgent need, worldwide, for improved contraceptives, especially male contraceptives. There is also an urgent need, worldwide, for improved prophylactic methods for preventing the spread of STDs. Vaccines could be highly valuable for meeting these needs and substantial efforts are being made to develop vaccines that will stimulate the body to synthesize its own antibodies against sperm and against STD pathogens. However, no contraceptive vaccine is yet available, and for some STDs, including AIDS, there is considerable doubt that a vaccine can ever be developed—infected individuals develop high titers of anti-HIV antibodies but this immunity to HIV does not stop the fatal course of AIDS.

In the absence of vaccines, the most effective methods now available for preventing both pregnancy and STDs are the condom, and the topical spermicidal contraceptives—foams, jellies, suppositories, and sponges. Condoms are both contraceptive and prophylactic since they create a mechanical barrier that prevents sperm as well as STD pathogens in the ejaculate from contacting the sexual partner. Many topical contraceptives are also both contraceptive and prophylactic since they use detergents for their active (spermicidal) ingredient, usually the nonionic detergent nonoxynol-9. Detergents not only kill (lyse) sperm, they also kill many pathogenic bacteria, protozoa, and viruses. Unfortunately, detergents also injure epithelial cells, and many people cannot use topical contraceptives because the detergents cause too much irritation, especially to the urethra. Also, detergents are only active for a short time after being applied to a mucus epithelium: contraceptive suppositories start to become unreliable about 45 minutes after being inserted in the vagina because detergents become inactive after solubilizing oily molecules. Detergents are also absorbed into the body through mucus epithelia.

If used properly, condoms as well as topical contraceptives are highly effective in preventing pregnancy and disease. However, numerous studies have shown that the reliability of both these methods is limited almost entirely by "user failure". That is, the condom is not put on in time, or not at all, or the suppository is inserted too early, too late, or not at all. Such "user failure" is usually due to the bother of using these prophylactic contraceptive methods—they require actions and interruptions inconsistent with sexual behavior. Moreover, topically applied detergents strongly inhibit most forms of oral sex, and condoms are often disliked by men because they interfere with foreplay, reduce the sensations of intercourse, and are a bother to remove, and dispose, postcoitally.

Thus there is a need, both for men and for women, for prophylactic contraceptives that are more reliable because they are less of a bother to use and require procedures more consistent with sexual activity. The most convenient and popular methods of contraception now available (the "pill", and intrauterine devices, IUDs,) provide little or no protection against STDs. Most users of these methods also need, and desire, protection against STDs, especially with the advent of AIDS.

Finally, many couples desire to conceive, and/or for religious or moral reasons do not wish to contracept, but they still need to protect each other from exchanging STDs. About one fourth of all infertile couples in the United States are infertile as a result of STDs, especially Chlamydia, an STD that is often asymptomatic and readily passes back and forth between two partners. There is thus a significant need for methods that are prophylactic against STDs but are not contraceptive. No such methods are now available.

OBJECTS OF THE INVENTION

It is a general object of this invention to provide contraceptive and/or prophylactic methods and compositions that overcome the problems inherent in the methods and compositions of the prior art by reducing the bother required in using the methods, by protecting more areas of skin and mucus epithelia at high risk for exchanging STD pathogens, and by enhancing the motivation for use by providing methods, compositions, and selections of active ingredients that more closely match all the needs and desires of individual users.

It is a specific object of this invention to create topical methods and compositions that treat, temporarily, the external surfaces of skin and mucus epithelia and do not entail the risks of delivering agents systemically (e.g., endocrine disorders that might be caused by steroidal or peptidal contraceptives, or immune disorders, including permanent infertility, that might be caused by contraceptive vaccines). Another related objective is to use as active ingredients highly specific molecules of the type naturally and abundantly present in all the mucus secretions of the body, namely antibodies, and to use these antibodies essentially as they are used by the body, by delivering to skin and mucus epithelia an appropriate selection of antibodies that will protect the user against pregnancy and/or disease.

It is another object of this invention to create a new contraceptive and/or prophylactic method for men consisting of a lotion to be applied to the external genitalia during sexual activity that includes a selection of antibodies against the sperm, toxins, and/or STD pathogens for which the user desires protection.

It is another object of this invention to create new, long-term contraceptive methods for women that will also be prophylactic: sustained release devices to be inserted in the uterus (IUDs), or in the vagina (IVDs), that release a selection of antibodies against sperm, toxins, and/or STD pathogens for which the user desires protection.

It is another object of this invention to create, for the first time, prophylactic methods for men and for women that are not contraceptive: lotions, vaginal suppositories, and IVDs that include a selection of antibodies against STD pathogens and/or toxins but no antibodies against sperm, the selection of antibodies being appropriate for individuals who simply desire protection against toxins and STDs.

It is another object of this invention to create new methods based on many of the existing contraceptive methods (such as IUDs, hormonal IVDs, and cervical caps) by making them prophylactic, as well as more reliable contraceptively, by incorporating in them sustained release devices that include a selection of antibodies appropriate for the user. Similarly, it is an object of this invention to improve many of the existing prophylactic contraceptives that use spermicides (such as suppositories, foams, jellies, sponge, and detergent-coated condoms) by including, in addition to the spermicide, a selection of antibodies appropriate for the user that will provide both longer lasting protection and better protection against spermicide-resistant STD pathogens and toxins.

It is a further object of this invention to provide contraceptive and/or prophylactic methods and compositions that are inexpensive enough to be used by individuals of all economic classes and yet, since these methods must be used repeatedly throughout the sexually active life of each individual, provide manufacturers strong profit incentives to reach the broadest possible markets.

The foregoing objects are achieved by the compositions, devices and methods of the present invention, detailed descriptions of which are given below.

SUMMARY OF THE INVENTION

Each embodiment of this invention includes a selection of one or more antibodies that best suits the desires of an individual user. For protection against the exchange of sperm (contraception) one or more antibodies that immobilize sperm in mucus are included. Similarly, for each toxin or STD pathogen for which protection is desired, one or more antibodies are included that will immobilize that toxin or STD pathogen in mucus. In each embodiment, enough of each antibody is included to deliver a dose sufficient to exert the desired immobilizing effect(s).

In one embodiment, suitable for men, the selection of antibodies desired by the user is incorporated in a pharmaceutically acceptable lotion to be applied, during sexual activity, to the external genitals and to any other area of skin or epithelium where protection against sperm, toxins, and/or STD pathogens is desired: The lotion can be directly applied by hand to all areas of skin in need of protection and indirectly by the penis and fingers to all internal mucus epithelial surfaces that may require protection (e.g., vagina, mouth, rectum).

In another embodiment, suitable for women, the selection of antibodies is incorporated in a sustained release device for insertion, and retention, in the vagina, an Intra-Vaginal Device, IVD, for the sustained release of the selection of antibodies desired by the user: such an IVD can readily be inserted, and removed by the user without the assistance of trained personnel.

In another embodiment suitable for women, the selection of antibodies is incorporated in a sustained release device for insertion and retention in the uterus, an Intra-Uterine Device, IUD, for the sustained release of the selection of antibodies desired by the user.

In another embodiment of the invention, the selection of antibodies desired by the user can be included in any of several existing contraceptive methods to enhance their contraceptive reliability and/or to add to them prophylactic efficacy against STDs and toxins e.g, sustained release devices for delivering the selection of antibodies can be incorporated in IUDs, IVDS, and cervical caps, including those devices that release hormones (e.g., progestins and estrogens) as active ingredients.

In another embodiment of the invention, the selection of antibodies desired by the user can be included in any of several detergent-based, or detergent-enhanced, prophylactic contraceptives similar to those now available, (e.g., vaginal suppositories, jellies, creams, tablets, and foams; diaphragm plus jelly, the "sponge", and detergent-coated condoms) to extend the duration of protection and to enhance protection against STD pathogens, especially detergent-resistant toxins and STD pathogens.

In yet another embodiment of this invention, existing detergent-based or detergent-enhanced topical and barrier contraceptives (e.g., vaginal suppositories, jellies, creams, tablets, and foams; diaphragm plus jelly, the "sponge", and condoms) can be converted to detergent-free methods for individuals who are highly irritated by detergents by substituting an appropriate selection of contraceptive and/or prophylactic antibodies for the detergent.

BRIEF DESCRIPTION OF THE DRAWINGS

FIG. 1 shows how "pan semen" antibodies agglutinate all motile sperm in semen. Human semen is shown before (control) and after adding threshold doses of MHS-8 and H6-3C4. All motile sperm present are permanently aggregated into clusters, and the clusters remain intact long after all sperm die.

DETAILED DESCRIPTION OF THE INVENTION

Figures 2, 3:
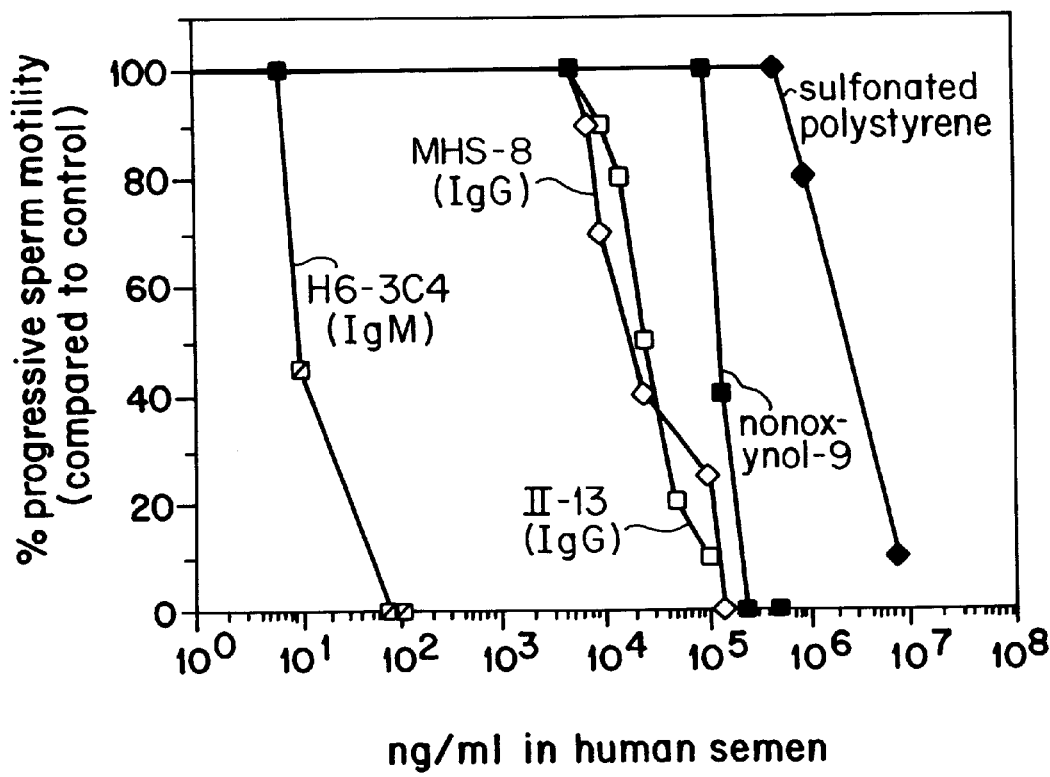
FIG. 2 shows the stability of "pan semen" antibodies when incubated in unsterile saline at room temperature, and in human semen, cervical mucus, and feces at body temperature (37° C.). Near-threshold concentrations of the antibodies were stored in these fluids, and at various times samples were withdrawn and tested with fresh samples of semen. The antibodies caused 100% agglutination of all motile sperm after being stored for the intervals indicated.
FIG. 3 compares the sperm-immobilizing concentrations of various agents when added to human semen. The vertical scale shows the per cent of sperm that remained progressively motile after adding the agents at the concentrations indicated by the logarithmic horizontal scale.

This invention relates to a method for immobilizing sperm, toxins, and/or STD pathogens in the mucus secretions shed by skin and mucus epithelia for purposes of contraception and/or prophylaxis. The method of the invention comprises using appropriately selected antibodies to immunize passively the surfaces of skin and mucus epithelia that are exposed to semen during sexual activity and/or that are most at risk of exposure to STD pathogens. The invention also relates to compositions and devices suitable for use in this method.

The present invention developed from our discoveries that:

1) antibodies can be produced that are capable of immobilizing sperm in semen and cervical mucus, despite the fact that human semen contains many immunosuppressive factors that protect ejaculated sperm from attack by the immune system (Witkin *Am. J. Reprod. Immunol.* 17:61–64 (1988); Alexander and Anderson *Fertil. Steril* 47(2):192–205 (1987); James and Hargreave *Immunol. Today* 5(12):357–363 (1984); Anderson and Tarter *J. Immunol.* 128(2):535–539 (1982); Sethi and Brandis *Eur. J. Immunol.* 10:964–965 (1980); Lord, Sensabaugh, and Stites *J. Immunol.* 118(5):1704–1711 (1977)), and despite the fact that most antisperm antibodies are not capable of inhibiting sperm motility in semen;

2) antibodies can be produced that are stable not only in human semen and cervical mucus but also in human feces, even though it is well-known that all these media contain many active proteases, especially semen (Mann and Lutwak-Mann *Male Reproductive Function and Semen* Springer-Verlag p. 495 (1981));

3) antibodies can be produced that are stable for prolonged periods of time at room temperatures in a wide range of pharmaceutically acceptable vehicles, despite the presence of detergents in such vehicles, and even if the antibodies are fully hydrated;

4) antibodies can be produced that are so potent at immobilizing sperm in mucus that contraceptively-reliable doses of antibodies can be delivered to the cervical region of the vagina using the penis as the "applicator" even though contraceptively-reliable doses of detergents cannot be delivered in this way without causing severe irritation to the urethra;

5) antibodies can be produced that are so potent at immobilizing in mucus secretions, sperm, toxins, and STD pathogens that despite the high cost of producing monoclonal antibodies, the required dose is so small that it is economically feasible to use these antibodies in inexpensive prophylactic contraceptives; and 6) antibodies can be produced that are "pan semen", that immobilize in mucus not only sperm but virtually all other cells contained in the ejaculate, including the white blood cells most likely to be carriers of AIDS and other STDs, even though such infected cells often escape detection by the immune system of the infected individual, and yet these "pan semen" antibodies are not likely to injure or immobilize cells not exposed to semen and hence may be delivered safely, over prolonged periods of time, to skin and mucus epithelia.

Systemically delivered antibodies have long been used to achieve temporary passive immunization, and more recently, orally administered antibodies have begun to be used for passive immunization of the gastrointestinal tract: orally administered antibodies that block adhesion sites on intestinal bacteria provide effective prophylaxis and therapy against infections caused by these bacteria in animals (P. L. Sadowski, U.S. Pat. No. 4,652,448) and also in humans, "traveler's diarrhea" (Tacket et al. *N. Engl. J. Med.* 318:1240–1243 (1988)). Oral administration of antibodies also has a well established biological basis: milk provides infants with the entire array of antibodies being produced and secreted by the mother. However, to the best of our knowledge, prior to the present invention, there has been no report describing or suggesting the use of antibodies for topical contraception and/or prophylaxis against STDs by applying the antibodies directly to the skin and mucus epithelia, or for using the penis as an "applicator" to deliver a contraceptively-reliable dose of antibodies to the cervical region of the vagina.

The guiding concept that led to the discoveries on which the present invention is based was to search for antibodies that immobilize sperm in semen and in cervical mucus, since: 1) there are clinical reports of infertile men whose semen contains anti-sperm antibodies that immobilize sperm, usually by agglutinating the sperm, and infertile women whose ovulatory mucus contains antisperm antibodies that immobilize sperm, usually by causing the sperm to shake in place, unable to progress; 2) if monoclonal antibodies with these sperm-immobilizing characteristics could be obtained, they could be used locally and topically for contraception simply by introducing them directly into the cervical region of the vagina; 3) such topically applied antibodies would be inherently low in risk to the user since few should enter the body and most would simply be shed along with the mucus secretions (cervical mucus, semen) to which they were delivered (indeed, skin and external mucus epithelia are continuously exposed to foreign proteins, and only rarely do they cause irritations or allergic responses; in contrast, systemic delivery of antibodies for passive immunization often causes "serum sickness" and other allergic reactions to foreign proteins); and 4) as was demonstrated in the development of the first reliable contraceptive suppository (Encare-Oval), the contraceptive efficacy of a topically applied agent can be extensively tested in women without placing them at risk of pregnancy by testing the agent in surgically-sterilized women and evaluating its effectiveness by examining postcoital samples of cervical mucus—if the agent is effective all sperm present will be immobilized, and no sperm will have entered the upper regions of the cervical canal.

We made an extensive search of the literature for all reports of monoclonal antisperm antibodies that might immobilize sperm in semen, and requested samples of these antibodies, and any others that might be useful, from investigators throughout the world. Most of these antisperm antibodies had little or no effect on sperm motility when tested in undiluted semen, but we found three antibodies that strongly agglutinate sperm in semen and also strongly immobilize sperm in ovulatory mucus by causing them to shake in place: II-13, H6-3C4, and MHS-8. Although not yet tested in ovulatory mucus, HS-80 and HS-85 also cause virtually all motile sperm in semen to agglutinate. (For pertinent literature on these and other antisperm antibodies see: (II-13) Mettler et al *Am. J. Reprod. Immunol.* 5:125–128 (1984); (H6-3C4) Isojima et al *J. Reprod. Immunol.* 10:67–78 (1987); (MHS-8) Herr et al *Biol. Reprod.* 32:695–711 (1985) and Herr et al *Biol. Reprod.* 35:773–784 (1986); (HSV80 and HSV-85) Menge et al *Am. J. Reprod. Immunol.* 13:108–114 (1987), and Lee et al *J. Reprod. Immunol.* 6:227–238 (1984). See also Anderson et al *Fertil. Steril.* 47(2):192–205 (1987).)

Typical results for the agglutinating effects of these antibodies are shown in FIG. 1.

To our surprise, we found that these antibodies are not degraded by the proteases in semen. The antibodies continue to immobilize sperm in semen and in cervical mucus for longer than the sperm remain alive—or about half a day in many of our in vitro experiments. To further assure ourselves that these antibodies are not rapidly degraded by the proteases or other factors in semen and in cervical mucus, we incubated the antibodies at 37° C. (body temperature) in semen and in ovulatory cervical mucus, and then tested them again with fresh samples of semen. FIG. 2 shows that under these conditions the antibodies remain stable for days to weeks. Postcoitally, most of the ejaculate is shed along with vaginal and cervical secretions within a few hours, and most cervical secretions during the ovulatory period are shed within about 1 day. Hence these antibodies, once delivered to the vagina, are likely to remain active for as long as they reside in the vagina.

To be economically feasible, and to be delivered in reliable concentrations to the cervix by the penis, antisperm antibodies used for topical contraception must be highly potent at immobilizing sperm in mucus. FIG. 3 shows the concentrations at which four different agents immobilize sperm in semen: H6-3C4, a decavalent IgM antibody; MHS-8, a bivalent IgG antibody; nonoxynol-9, the detergent used in many topical contraceptives; and sulfonated polystyrene (1,200,000 MW), a polymer that binds nonspecifically to many cells and pathogens and is being tested for use as a prophylactic contraceptive as well as for systemic prophylaxis against AIDS. The results shown in FIG. 3 demonstrate that antisperm IgM antibodies like H6-3C4 can immobilize all sperm in semen at less than 100 ng/ml, a sperm-immobilizing potency 1000× the potency of nonoxynol-9, and 10,000× the potency of sulfonated polystyrene.

The antibodies included in FIG. 3 have similar potencies for immobilizing sperm in both semen and cervical mucus. However, they immobilize sperm by two different mechanisms: in liquified semen, the antibodies create permanent crosslinks between sperm, causing the sperm to agglutinate in large clusters that have no forward motility even though the sperm flagella continue to beat vigorously. The antibodies also create adhesive crosslinks between sperm and mucins, the large highly branched glycoproteins that create the viscoelasticity of mucus. In ovulatory cervical mucus, these sperm-mucin crosslinks create such a large viscoelastic drag that sperm can only shake in place and make no forward progress. (If the mucins become too dilute or degraded, as occurs during the liquefaction of semen, some of the shaking sperm begin to move forward but then they collide with other sperm, and these collisions enable the antibodies to form sperm-sperm crosslinks that agglutinate all the forwardly motile sperm.)

The observations in FIG. 3 are the first to demonstrate the extraordinary potency of antibodies for immobilizing sperm in mucus. It is widely appreciated by immunologists that a single IgM molecule bound to a red blood cell can trigger the complement system to lyse the cell, but in semen, the complement system is strongly inhibited (see review by Alexander and Anderson *Fertil Steril.* 47(2):192–205 (1987)). The number of antibody molecules needed to immobilize a motile cell in mucus secretions has not, to our knowledge, been previously reported. (Isojima et al *J. Reprod. Immunol.* 10:67–78 (1987), emphasize the potency of H6-3C4 to kill sperm by activating the complement system, but only if exogenous complement has been added to a dilute suspension of sperm, and, if the sperm have been diluted in saline without adding the complement system, by causing the sperm to agglutinate. However they do not report testing the sperm-immobilizing potency of H6-3C4 in semen or in ovulatory mucus.) Our observations of H6-3C4 demonstrate that in semen a few hundred molecules per sperm cell causes permanent immobilization, and that each permanent cross-link between sperm cells can be created by a single IgM molecule. The fact that the forces exerted by a vigorously motile sperm cell are too small to break even a single antibody-antigen bond has just recently been reported (Baltz, Katz, and Cone *Biophys. J.* 54(4): 643–654 (1988)). Since most STD pathogens are much smaller than sperm, this result also implies that most STD pathogens can be immobilized by even fewer antibody molecules. Thus, our results reveal that sperm and most STD pathogens will become permanently immobilized in mucus when they bind on the order of 10–100 molecules of IgM.

IgM molecules are decavalent, with 10 antibody-antigen binding sites per molecule. In contrast, IgG molecules are bivalent. FIG. 3 shows that H6-3C4, an IgM, is about 1000 times more potent at immobilizing sperm than is MHS-8, an IgG. Increasing the number of binding sites/molecule greatly increases the effective affinity (the "avidity") of an antibody, and once an IgM molecule binds to a cell it rarely comes off. Thus polyvalent IgM and IgA molecules can immobilize pathogens in mucus at much lower concentrations than can IgG. This is important for the secretory immune system since fewer polyvalent IgM and IgA molecules need be secreted to provide protection against each type of pathogen. Similarly, for topical prophylaxis and contraception, an IgM antibody like H6-3C4 is more economically feasible than an IgG antibody, which requires a 1000 fold greater dose.

It is widely believed by immunologists that the major role of secreted antibodies is to block the adhesive groups that enable a pathogen to adhere to its target cell, and the ability of such "adhesion-blocking" antibodies to protect against infection is well established (U.S. Pat. No. 4,652,448). What has not yet been appreciated is that each pathogen has so many adhesive sites that to block the adhesion between a pathogen and its target cell can require 1000s to 100,000s of antibody molecules per pathogen, many orders of magnitude more antibody molecules than are needed to simply, and permanently, immobilize the pathogen in mucus secretions.

Thus our observations on sperm-immobilizing antibodies have led us to realize that the most prevalent types of antibodies in mucus secretions, IgA and IgM, help create an extraordinarily potent first line of defense against motile pathogens simply by mechanically immobilizing these pathogens in mucus.

The most serendipitous finding in our search for antibodies that immobilize sperm in semen was discovering "pan semen" antibodies, antibodies that not only immobilize sperm in semen but also immobilize virtually all other cells in semen by coagglutinating them with the sperm. Each human ejaculate contains not only about $10^8$ sperm but also on the order of $10^6$ white blood cells and other germ-line and epithelial cells shed by various regions of the male reproductive tract. Many of these non-sperm cells can harbor viruses and other STD pathogens and can transmit these STD pathogens to the receptive sexual partner. Macrophage cells in particular are likely carriers for Herpes, Chlamydia, cervical cancer, and AIDS. Many of these infected cells escape being detected by the immune system of the infected individual. Especially in the case of AIDS, despite high titers of circulating anti-HIV antibodies, the disease progresses, and many surviving white blood cells either harbor the HIV genome and/or, complete HIV. Thus, prophylaxis against some of the most prevalent STDs, and prophylaxis against AIDS, requires blocking the exchange between sexual partners of infected white blood cells that even the infected individual's own immune system is unable to attack.

Figure 4A:
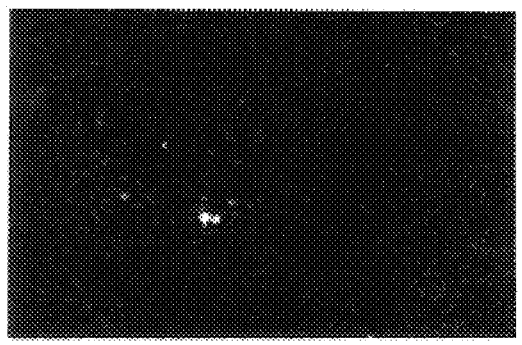
FIG. 4 shows how a "pan semen" antibody, H6-3C4, coagglutinates sperm with other cells in the ejaculate. In this figure, the cell that engulfed two fluorescent microspheres is a macrophage, one of the most likely types of cells for the sexual transmission of AIDS.
Figure 4B:
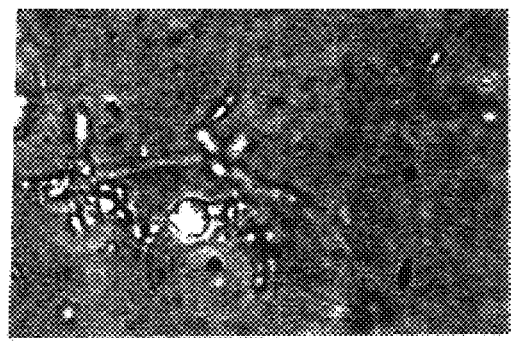

FIG. 4 shows how a "pan semen" antibody, H6-3C4, coagglutinates macrophages and sperm in semen. The macrophages were labeled by adding to the semen fluorescent latex spheres that these cells readily engulf. The cells coagglutinated with sperm remain so until long after the sperm have died, and thus will be shed postcoitally along with the agglutinated sperm. Since "pan semen" antibodies can immobilize in semen virtually all cells in the ejaculate that can potentially harbor STD pathogens, these antibodies can block the ability of these cells to enter, and infect, the mucus epithelia of the host.

All five antibodies we have tested that strongly agglutinate sperm in semen (II-13, H6-3C4, MHS-8, HS-80, and HS-85) also cause coagglutination of virtually all cells present in semen. Thus all five of these are "pan semen" antibodies. At least three of these, II-13, MHS-8, and H6-3C4, do not bind directly to sperm, but instead bind to factors secreted by the seminal vesicles (Isojima et al *J. Reprod. Immunol.* 10:67–78 (1987)). During the process of ejaculation these seminal vesicle factors mix with and coat (adsorb to) virtually all cells in the ejaculate. Thus any antibody that binds to the surface coating antigens secreted by the seminal vesicles can be expected to immobilize in mucus virtually all cells in the ejaculate.

The seminal vesicle factor to which H6-3C4 binds is specific to semen and the seminal vesicles (Isojima et al *J. Reprod. Immunol.* 10:67–78 (1987)) and thus, antibodies against this factor can be present in the blood without harming the individual, other than rendering them infertile. Indeed, H6-3C4 was obtained by cloning lymphocytes from an infertile woman who shows no other abnormality from the presence of this antibody in her blood other than infertility. Also, many infertile men and women who are otherwise healthy have high systemic levels of antisperm antibodies. Therefore, topical (external, nonsystemic) applications of "pan semen" antibodies that bind to surface coating antigens secreted by and specific to the reproductive tract are likely to cause little if any irritation or toxicity.

In addition to the surface coating antigens secreted by the seminal vesicles, other surface coating antigens may well be secreted by the vagina, by skin, and by other mucus epithelia in both males and females, and antibodies against such surface coating antigens might also immobilize in mucus not only sperm but many of the other cells in the ejaculate and/or cervical and vaginal secretions. Such antibodies might well prove useful not only for contraception but also for prophylaxis against many types of pathogens, especially those that can be harbored by white blood cells and other cells shed into mucus secretions. (Similarly, it may be possible in the future to develop vaccines that stimulate the immune system to secrete "pan semen" antibodies. Such vaccines should not only protect females against pregnancy but also against STD pathogens harbored in virtually all cells that are shed into, and mixed with, semen and cervical mucus.)

Antibody Selection. The present invention is not based on the use of any particular antibody. Instead, this invention relates, at least in part, to methods for selecting and/or developing antibodies that can be used in new and unexpected ways to provide topical contraception and/or prophylaxis against STDs.

Many monoclonal antibodies are already available that bind selectively to a wide range of STD pathogens and many of these are now used routinely for clinical diagnosis to determine whether or not particular STD pathogens are present in semen, blood, or other fluids. It will be evident from a reading of the present disclosure that many of these antibodies can be used for prophylaxis against STDS, not just diagnosis.

To obtain antibodies satisfactory for use in the present invention, the following criteria and aims must be met.

1) The antibodies must function in semen and ovulatory mucus. Most antisperm antibodies do not satisfy this condition. Since most components of the immune system are often missing in mucus secretions, the preferred antibodies must also be capable of immobilizing sperm, toxins, and/or STD pathogens in mucus without requiring the presence of complement or any cellular components of the immune system.

2) The preferred antibodies must have high avidity for the target cell or molecule since only with such antibodies can the applied dose be small enough to be economically, and practically, feasible. The two types of antibodies most abundant in mucus secretions, IgA and IgM, are highly polyvalent and hence usually have much higher avidities for their targets than IgG, the most prevalent antibody in serum. Hence the preferred antibodies for this invention are polyvalent IgA and IgM, since such antibodies can immobilize sperm and other cells in mucus at doses below 100 ng/ml. However, IgG antibodies with high-affinity binding sites may also prove useful, especially for toxins and small nonmotile pathogens such as viruses.

(Antibodies that block the adhesion sites which form attachments between sperm and egg, or between STD pathogens and their target cells, may also be useful and such "antiadhesin" antibodies are described in U.S. Pat. No. 4,652,448 and U.S. Pat. No. 4,731,245. However, the protective dose for such antibodies is likely to be much larger, and it is difficult to test the efficacy of such antibodies in vivo without placing individuals at risk of pregnancy or infection whereas antibodies that immobilize their target cells in mucus can be tested directly for efficacy in mucus secretions.)

3) The preferred antibodies must be stable in semen and in cervical mucus, and not subject to rapid degradation by the proteases and immunosuppressive factors in these fluids. Also, the antibodies must not be degraded by STD pathogens. For example, N. gonorrhea releases proteases that specifically degrade human IgA1 type antibodies, but do not degrade IgA2 antibodies. Antibodies derived from other species may be particularly useful in meeting this requirement since most STD pathogens are species specific.

4) The preferred antibodies should be specific for sperm, toxins, and/or STD pathogens and must not cross-react with other cells or tissues of the body, to any unacceptable extent. Such antibodies, should they enter the body through breaks in the skin or epithelia, will be unlikely to cause adverse effects. Similarly, the preferred antibodies must be essentially non-allergenic and non-irritating when repeatedly delivered to the skin, mucus epithelia, or systemic circulation. The antibodies are, advantageously, monoclonal.

5) Since host cells that harbor STD pathogens are themselves STD pathogens, preferred antibodies against these host cells must be especially carefully chosen to be nontoxic to the host. "Pan semen" antibodies such as II-13, MHS-8, H6-3C4 that bind to cell-surface antigens secreted into the reproductive tract and that immobilize virtually all cells in semen are an example of the types of antibodies that can be used to immobilize in mucus secretions all host cells that may harbor STD pathogens while at the same time being unlikely to cause irritation or toxicity to normal host cells elsewhere in the body.

6) Antibodies to be used in the present invention should be suited to the needs of the user and appropriate to achieve the highest levels of protection. Indeed, a fundamental property of the secretory immune system is that it continuously secretes an enormous number of different antibodies and thereby provides protection against nearly all pathogens to which the skin and epithelia are likely to be exposed. Similarly, a fundamental concept in this invention is to deliver to the skin and mucus epithelia a selection of antibodies that best suits each user's desires for protection. The preferred selection of antibodies will thus depend on where the user lives, the user's sexual practices, partners, age, intentions, previous infections, and fears. Also, as is often the case in the secretory immune system, more than one type of antibody against a single target cell or molecule may be needed to achieve the level of protection required: many pathogens (like HIV) rapidly change their antigenic surfaces and any given antibody may not bind to all forms of the pathogen. Finally, if several different antibodies are present, it is less likely that the pathogen to which they bind can simultaneously overcome or degrade all of them.

Antibodies suitable for use in the present invention can be obtained using processes well known in the art. For example, the antibodies can be obtained from the blood, milk, or other mucus secretions of animals immunized against sperm, toxins, and/or STD pathogens. Similarly, monoclonal antibodies suitable for use in the invention can be obtained, for example, by cloning lymphocytes from infertile animals that are immune to sperm and from animals that are immune, or have been actively immunized against sperm, toxins, and/or STD pathogens. To minimize their potential for causing irritation and/or allergic reactions, and to maximize their potency to immobilize and/or agglutinate, the monoclonal antibodies are, advantageously, derived from cells from the same species of animal for which they will be used.

For pathogens and toxins for which it is difficult to obtain suitable monoclonal antibodies from cell lines derived from the same species (since pathogens endemic to a species sometimes evolve mechanisms for inactivating the antibodies synthesized by that species), monoclonal antibodies derived from cell lines of other species are suitable.

Antibodies suitable for use in the present invention (whether produced, for example, from the milk or blood of immunized animals, by cell culture, ascites tumors, or genetically transformed or transgenic organisms such as bacteria, yeast, or animals), are made pharmaceutically acceptable prior to being delivered to or applied to the skin or epithelium. This process can include any suitable method for purification, sterilization, and testing for uniformity, activity, and toxicity. The antibodies can also be chemically altered, for example, to change the composition or structures of the sugar residues attached thereto. They can be used in the form they typically have in serum, or they can include the modifications that occur when antibodies are secreted into the mucus, that is, they may be combined with the secretory components that adhere to secreted antibodies.

Such molecular modifications of the antibodies are not required for the method of invention to be effective. Rather, such modifications can be used to enhance the shelf-life, active life, or potency, or to reduce the potential for irritation or allergic reactions, or to reduce the cost of production.

The antibodies suitable for use in the present invention can be applied, for example, as a composition that includes any suitable pharmaceutically acceptable carrier that does not denature or inactivate them. The composition, comprising antibody and carrier, can take the form, for example, of a lotion, cream, gel or suppository. Consistency, color, odor, and taste of the composition can all be varied to attain maximum desirability. Additional active ingredients can also be included in the composition to provide protection against pathogens for which there are no available antibodies, or as an adjunct to the antibodies. These include, but are not limited to, broad-spectrum cytotoxic agents (e.g., chlorhexidine, and detergents like benzalkonium chloride and nonoxynol-9) as well as broad-spectrum cytostatic agents that immobilize or adhere nonspecifically to cells and pathogens (e.g., sulfonated polystyrenes (C. D. Szymanski, U.S. Pat. No. 4,432,967), dextran sulfate, or other polymers that adsorb to many types of pathogens). In addition, agents specific for a given pathogen can also be included. For example, molecules that bind to and block the target-cell receptor sites on the pathogen that enable it to adhere to and infect its target cells (e.g., in vitro experiments have shown that low concentrations of CD4 molecules bind to the target-cell receptors of HIV and prevent HIV from infecting target cells).

Agents that thicken ovulatory mucus (making it impenetrable to sperm and many motile STD pathogens) such as starch or other water-absorbing agents, antimucin antibodies, or other mucin cross-linking agents can also be added as can progestins or other hormonal agents that cause the cervical epithelium to secrete mucus that is impenetrable to sperm and many motile STD pathogens.

Agents that help regulate (buffer) the concentration of free ions such as iron (e.g., lactoferrin), hydrogen, and/or zinc can also be included to help regulate vaginal flora.

For prophylaxis against STDs, a lotion (or similarly, a cream or gel, etc.) containing an appropriate selection of antibodies can be applied to all areas of skin likely to come in intimate contact during sexual activity, and especially to any area that has sores or breaks in the skin. Unlike the limited areas of skin and epithelia protected by condoms and topical contraceptives, lotions (or the like) containing antibodies suitable for use in the method of the present invention can protect many areas of skin in addition to the surfaces of the penis and the upper vagina, such as the inner and outer lips of the vulva, the base of the penis and scrotum, the inner thighs and pubic and perianal regions. Important for the prevention of AIDS, for anal intercourse, the lotion can also be applied directly to the anus and can be delivered to the rectum via the penis.

Using fluorescently labeled test lotions, we have found that the concentrations of antibodies needed for reliable contraception and prophylaxis can readily be applied to the cervical region of the vagina, and the inner region of the rectum, by applying sufficient lotion (or the like) to the penis and then using the penis as an "applicator". For vaginal intercourse, approximately 10 to 100 times more antibody needs to be applied to the penis than if the entire dose of antibody were delivered directly to the upper vagina, as with a suppository.

The concentration of antibodies to be included in the compositions of this invention and the total dose to be administered can readily be determined by one skilled in the art using known methods. Since most STD pathogens are rarely delivered to an epithelium at a concentration comparable to sperm in semen, smaller doses of antibodies are required for prophylaxis than for contraception. Therefore, a large number of different antibodies can also be included in, for example, a lotion, to provide protection against a wide range of STD pathogens at little additional cost.

Antibodies suitable for use in the method of this invention can also be incorporated into an intravaginal device (IVD) for the sustained release of antibodies into the upper vagina to maintain continuous contraceptive and/or prophylactic protection for as long as the device remains functioning and in place. The user can insert and remove such IVD at any time of her choice and she need not seek or require assistance or supervision from trained personnel.

In one embodiment, copolymers of ethylenevinyl acetate, which forms a soft, rubber-like material, are loaded, prior to polymerization, with antibodies suitable for use in the method of this invention in the form of a dry powder (Langer and Folkman, 1976; U.S. Pat. No. 4,391,797). The powder forms tortuous channels in the polymer through which water may enter, dissolve the antibodies, and permit them to diffuse slowly out of the device. By suitably adjusting the mass ratio of antibodies to copolymer, any desired release rate can be achieved. For example, to provide protection for more than the duration of a typical menstrual cycle, the mass ratio of dry powder to copolymer can be about 1:1 to 1:2, since at about these ratios the device will release about ½ of the antibodies contained in it over the course of 1 month. To be easily inserted and withdrawn from the vagina, and to be retained reliably within the vagina for as long as desired, the copolymer can be molded, for example, into the shape of a ring about 2–3 inches in widest diameter, and about ¼–⅜ inch in cross-sectional diameter. One skilled in the art will appreciate that as the upper vagina is distensible, the shape and size of a satisfactory intravaginal device can be highly variable (U.S. Pat. Nos. 4,304,226; 4,066,075; 4,292,965). The total dose of antibody to be released by the above-described IVD depends on the amount of the antibody that must be present and active in the vagina for reliable contraception and/or prophylaxis, and the lifetime or residence time of the antibody once it is released by the device into the vagina. For example for contraception and prophylaxis against AIDS using H6-3C4, no more than about 10 $\mu$g need be present and active in the vagina. This antibody is stable for about a week when incubated at 37° C. in human ovulatory cervical mucus and in human semen. In contrast, ovulatory cervical mucus flows out of the vagina in less than a day. Hence, this monoclonal antibody is likely to remain active for as long as it resides in the vagina, which, during midcycle, will be about 1 day. Therefore, the device need release no more than about 10 $\mu$g/day which implies that the total dose loaded into the device need be no more than 100 days times 10 $\mu$g/day, or less than 1 mg of H6-3C4 per IVD. Each device can readily contain far more than this. A device with a mass of 10 g can hold more than 3000 mg of the antibody, a large enough supply for the life span of the user. In addition, the device can contain a large number of other antibodies selected to satisfy the desires of the user for prophylaxis against many different toxins and STD pathogens.

Antibodies suitable for use in the method of the present invention can also be included in an intrauterine device (IUD) to enhance the contraceptive efficiency of the IUD as well as to provide an IUD that protects the user against STDs.

As discussed above for vaginal devices, the dose of antibodies required for the sustained release of effective concentrations of antibodies is so small that they can easily be incorporated in an IUD composed of the same or similar ingredients as the vaginal devices. The incorporation of 1 gm of an antibody such as H6-3C4 into a an IUD made with copolymers of ethylene-vinyl acetate at a mass ratio of dry powder to polymer of about 1:2 to 1:3, results in an IUD that potentially can continuously release contraceptively effective doses of the antibody for longer than 30 years, or longer than the reproductive life-span of a women. The device can also contain a selection of antibodies sufficient to provide continuous protection against many toxins and STD pathogens for similar extended periods of time.

As with vaginal devices, the size, shape, and composition of an IUD can be highly variable. Almost any object that has been inserted into the uterus and has a shape that helps it remain in place has been found to be contraceptively effective. Thus any size or shape comparable to existing IUDs should be satisfactory. Also, any pharmaceutically acceptable material capable of the sustained release of antibodies should be satisfactory, including bioerodable materials that will eliminate the need to remove the IUD at the end of its active life.

A "marker" string is attached to most IUDs to enable the user to determine whether her IUD is still in place. The string protrudes from the cervical opening in the vagina and can be readily felt using a finger. However, the string can enable pathogens to ascend through the cervical canal, escaping this major site of immunosurveillance, and initiating pelvic inflammations (Tatum, et al JAMA 231:711–719 1975). In addition, should the IUD fail to prevent a pregnancy, the marker string, with any associated pathogens, is drawn through the cervical canal into the uterus as the uterus enlarges during midgestation. In contrast, there is no need for a "marker" string for an antibody-releasing IUD as provided by this invention since the user can test for the presence of the IUD, as well as its proper functioning, by testing for the presence of adequate concentrations of the appropriate antibodies in her cervical mucus. Test kits for home use for this purpose can easily be designed and produced with readily available methods.

The contraceptive efficacy of IUDs as well as vaginal devices, like the lotion-type compositions described above, can be clinically tested in surgically sterilized women without putting them at risk of pregnancy. Postcoital samples of ovulatory mucus at midcycle can be examined for the presence of sperm. If the antibodies are effective, all sperm in the cervical regions of the vagina should be immobilized, and no sperm should be present in the upper cervical canal. Similarly, the presence of immobilizing doses of anti-STD pathogen antibodies can be tested in mucus samples withdrawn from the uterus, again without placing the woman at risk of infection.

As described above with respect to the lotion-like compositions, the IVD and IUD sustained release devices of this invention can also include the broad-spectrum cytocidal agents listed above, as well as antibodies and cytocidal agents against local (vaginal and uterine) flora that may help prolong the useful life of the devices.

It will be clear to one skilled in the art that the contraceptive and prophylactic methods (and compositions and devices) of the present invention are applicable not only to humans but to other mammals as well, particularly domestic animals and rare or exotic zoo animals.

Systemic passive immunization with antibodies often provides therapeutic effects as well as prophylaxis, and it is to be expected that the antibodies delivered by the methods of this invention will in many cases provide therapeutic benefits in addition to contraception and/or prophylaxis.

For purposes of completing the background description and present disclosure, the entire contents of each of the published articles identified in this specification are hereby incorporated by reference into the specification and are relied upon.

The foregoing invention has been described in some detail for purposes of clarity and understanding. It will be clear to one skilled in the art from reading the present disclosure that the instant invention provides a means by which all presently available topical contraceptives can be converted into detergent-free methods. Suppositories, tablets, foams, jellies, creams, "The Sponge", and condoms can all be supplied with appropriate antisperm antibodies as the active agent instead of the detergents. Appropriate selections of antibodies against STD pathogens can also be added to provide protection against STDs. It will also be apparent that the prophylactic and contraceptive efficacy of condoms can also be enhanced by adding appropriate antibodies to the coating. It will also be obvious that various combinations in form and detail can be made without departing from the scope of the invention.

What is claimed is:

1. A pharmaceutical composition for passively immunizing skin surfaces and mucus epithelial surfaces against sperm comprising:
   i) at least one pan semen antibody capable of binding, directly or indirectly, to and thereby trapping said sperm; and
   ii) a pharmaceutically acceptable carrier, wherein said antibody is present in an amount sufficient to exert said trapping effect on said sperm and wherein said binding is direct or indirect, under conditions such that contraception is effected.

2. A pharmaceutical composition for passively immunizing skin surfaces and mucus epithelial surfaces comprising:
   i) at least one pan semen antibody capable of binding, directly or indirectly, to pathogens in semen and/or cells in semen, thereby trapping pathogens and/or cells in mucus secretions present on said skin or mucus epithelial surfaces; and
   ii) a pharmaceutically acceptable carrier,
wherein said at least one antibody is present in an amount sufficient to effect such trapping.

3. A pharmaceutical composition for passively immunizing skin surfaces and mucus epithelial surfaces of a mammal comprising:
   i) at least one antibody capable of binding directly or indirectly to a mammalian factor produced by said mammal and present on the surface of cells and/or pathogens in mucus secretions from said skin or mucus epithelial surfaces, thereby excluding said cells and/or pathogens from entering the body; and
   ii) a pharmaceutically acceptable carrier,
wherein said antibody is present in an amount sufficient to exert said excluding effect.

4. The composition according to claim 3 wherein said epithelium is selected from the group consisting of skin, gastrointestinal tract, respiratory tract and ocular mucosa.

5. The composition according to claim 3 wherein said epithelium is skin.

6. The composition according to claim 3 wherein said epithelium is gastrointestinal tract.

7. The composition according to claim 3 wherein said epithelium is respiratory tract.

8. The composition according to claim 3 wherein said epithelium is ocular mucosa.

9. The composition according to claim 1 wherein said carrier is a biologically compatible prolonged release carrier.

10. The composition according to claim 2 wherein said carrier is a biologically compatible prolonged release carrier.

11. The composition according to claim 1 wherein said carrier is a biologically compatible prolonged release carrier.

12. The composition of claim 1 wherein said pan semen antibody is selected from the group consisting of II-13, H6-3C4, MHS-8, HS-80 and HS-85.

* * * * *